US00PP34364P2

(12) United States Plant Patent
Hansen

(10) Patent No.: US PP34,364 P2
(45) Date of Patent: Jun. 21, 2022

(54) **X *MANGAVE* PLANT NAMED 'MAVERICK'**

(50) Latin Name: **x *Mangave* times x *Mangave* hybrid**
Varietal Denomination: Maverick

(71) Applicant: Hans A Hansen, Zeeland, MI (US)

(72) Inventor: Hans A Hansen, Zeeland, MI (US)

(73) Assignee: Walters Gardens Inc., Zeeland, MI (US)

( * ) Notice: Subject to any disclaimer, the term of this patent is extended or adjusted under 35 U.S.C. 154(b) by 0 days.

(21) Appl. No.: 17/803,135

(22) Filed: Mar. 1, 2022

(51) Int. Cl.
*A01H 5/12* (2018.01)
*A01H 6/00* (2018.01)

(52) U.S. Cl.
USPC ..... Plt./373

(58) Field of Classification Search
USPC ..... Plt./373

CPC ... A01H 5/12; A01H 5/00; A01H 5/02; A01H 6/00; A01H 6/12
See application file for complete search history.

(56) References Cited

U.S. PATENT DOCUMENTS

PP33,166 P2 * 6/2021 Hansen ..... Plt./373

* cited by examiner

*Primary Examiner* — June Hwu

(57) ABSTRACT

A new and unique X *Mangave* plant named 'Maverick' characterized by compact mounded habit of numerous lanceolate leaves with dense, overlapping, dark, greyed-purple spotting in strong ultraviolet light exposure. The new plant has numerous chartreuse flowers on dense, tall, stiff, highly branched scapes. The foliage has small, semi-flexible, marginal teeth and flexible to sharp apical mucro. The new plant is suitable as a potted houseplant plant, as a container plant for the patio or garden and for the garden or planted in the landscape, and the flowers are loaded with nectar for attracting hummingbirds.

2 Drawing Sheets

Botanical classification: x *Mangave* times x *Mangave* hybrid.

Variety denomination: 'Maverick'.

STATEMENT REGARDING PRIOR DISCLOSURES UNDER 37 CFR 1.77(b)(6)

The first non-enabling public disclosure of x *Mangave* 'Maverick' was on Mar. 1, 2021 with a brief description and photo on a website operated by Walters Gardens, Inc. This was followed by a brief description and photograph in the "Walters Gardens 2021-2022 Catalog" which was first distributed on May 21, 2021. Information for this website and catalog was obtained from the inventor. The first disclosure of the claimed plant, in the form of a sale, is planned to be made by Walters Gardens, Inc. on Feb. 28, 2022 to Legacy Gardens, LLC. All plants and information on 'Maverick' have been provided by the inventor. No plants of x *Mangave* 'Maverick' have been sold, in this country or anywhere in the world, nor has any disclosure of the new plant been made, more than one year prior the filing date of this application, and such sale or disclosure within one year was either derived directly or indirectly from the inventor.

BACKGROUND OF THE INVENTION

The present invention relates to the new and distinct x *Mangave* plant, x *Mangave* 'Maverick' hybridized on Oct. 17, 2014 by the inventor at a wholesale perennial nursery in Zeeland, Mich., USA as a cross between the proprietary unreleased hybrid known only by the breeder code x *Mangave* 11-2-4 (not patented) as the female or seed parent and x *Mangave* 'Bloodspot' (not patented) as the male or pollen parent. Through trials at the same nursery the plant was referred to by the code 15-34-23. The new plant has been successfully asexually propagated initially by division of offsets in 2018 followed by shoot tip tissue culture at the same nursery in Zeeland, Mich. These asexual propagation systems have been found to produce stable and identical plants that maintain all the unique characteristics of the original plant in successive generations.

BRIEF SUMMARY OF THE INVENTION x *Mangave* 'Maverick' differs from its parents as well as all other *Manfreda, Agave* and x *Mangave* known to the applicant. The most similar known x *Mangave* cultivars known to the inventor are: 'Blazing Saddles' U.S. Plant Pat. No. 31,274, 'Fiercely Fabulous' U.S. Plant Pat. No. 33,166, 'Inkblot' U.S. Plant Pat. No. 29,431, 'Moonglow' U.S. Plant Pat. No. 29,195 and 'Thunderbird' U.S. Plant Pat. No. 31,248.

'Blazing Saddles' has a smaller habit with narrower leaves that are more densely spotted with reddish coloration. 'Fiercely Fabulous' has broader leaves that are more upright in habit, or gray-green color with burgundy spotting and larger teeth. 'Inkblot' has a similar habit but the foliage is wider, more glaucous with smoky-purple color and purple-lavender spots with less total coverage. 'Moonglow' has a more silvery blue-green leaf surface with dark purple spotting. 'Thunderbird' is smaller and more upright in habit with leaves that are shorter and more completely covered with dark red spots.

The female parent, 11-2-4, has much wider and longer leaves with smaller teeth, the dark leaf spots are larger and more separated, and there are fewer leaves per mature plant.

The male plant has shorter leaves and is a smaller more compact plant, the apical spines marginal teeth are larger and firmer and the margin is distinctly darker brown.

The new plant, 'Maverick', is unique from all *Agave*, X *Mangave* and *Manfreda* known to the inventor by the following combined traits:

1. Compact mounded habit with numerous leaves at flowering;
2. Leaves lanceolate and dense, overlapping, dark, greyed-purple spotting in high light exposure;
3. Foliage with small, sharp, firm, marginal teeth and semi-flexible sharp apical mucro;
4. Moderate to rapid growth rate;
5. Numerous chartreuse flowers on dense, stiff, tall, highly branched scapes.

BRIEF DESCRIPTION OF THE DRAWINGS

The photograph of the new plant demonstrates the overall appearance of the new plant including the unique traits grown with supplemental water and fertilizer as needed. The colors are as accurate as reasonably possible with color reproductions. Ambient light spectrum, temperature, source and direction may cause the appearance of minor variation in color.

DETAILED BOTANICAL DESCRIPTION

Figure 1:
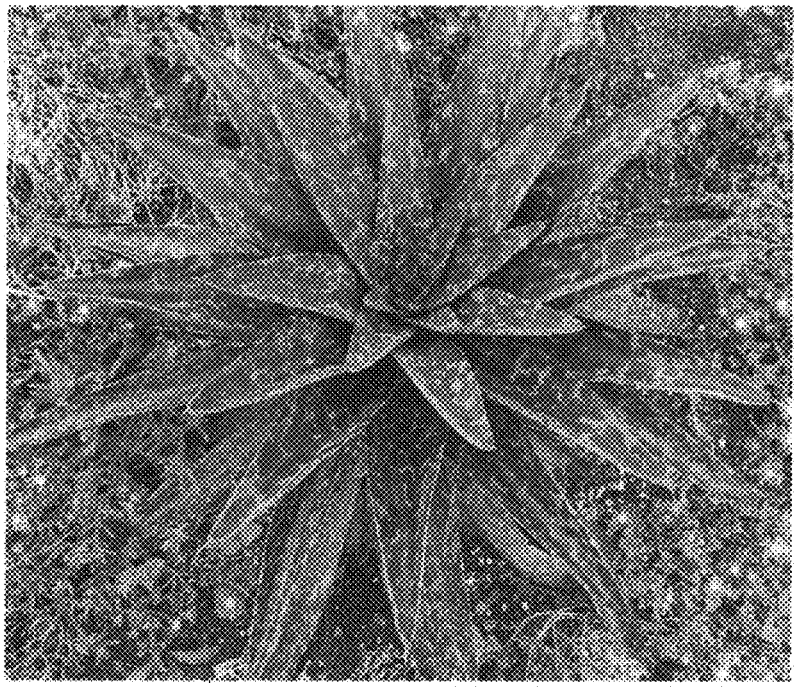
FIG. 1 shows a three-year-old plant from above as grown the last season in a full-sun trial garden.
Figure 2:
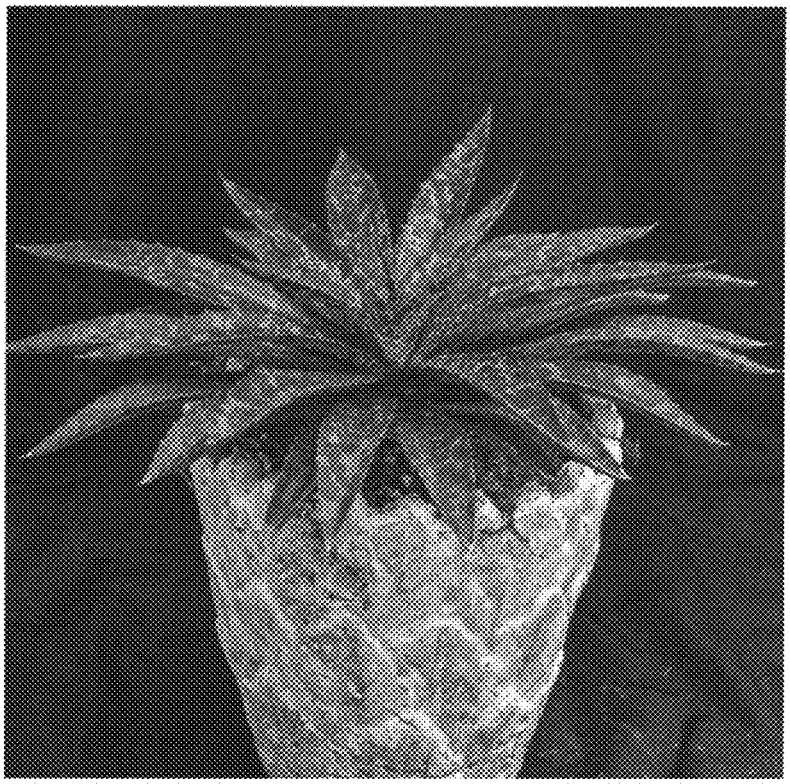
FIG. 2 shows a side view of a two-year-old plant in a container with the last season in a full-sun trial garden.
Figure 3:
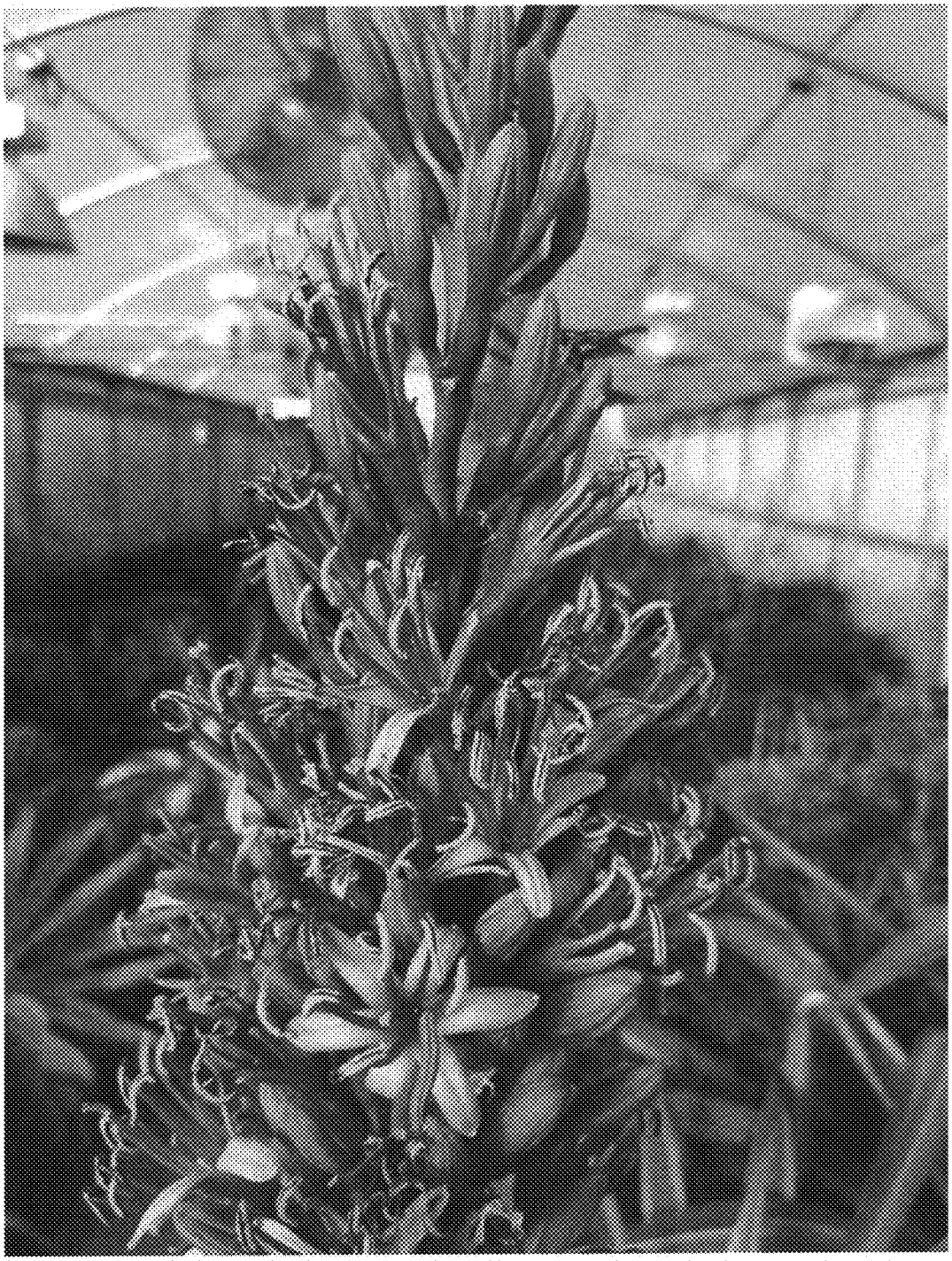
FIG. 3 shows the distal flowers and buds on a three-year-old plant in the greenhouse.

The following descriptions and color references are based on the 2015 edition of The Royal Horticultural Society Colour Chart except where common dictionary terms are used. The new plant, X *Mangave* 'Maverick', has not been observed under all possible environments. The phenotype may vary slightly with different environmental conditions, such as temperature, light, fertility, moisture and maturity levels, but without any change in the genotype. The following observations and size descriptions are of three and four-year old plants in a commercial wholesale greenhouse and in a full-sun trial garden in Zeeland, Mich. with supplemental water and fertilizer as needed.

Botanical classification: x *Mangave* hybrid (*Manfreda* x *Agave*);

Parentage: The female or seed parent is the proprietary hybrid 11-4-2 and the male or pollen parent is 'Bloodspot';

Propagation: Division and sterile plant tissue culture;

Time to initiate roots from tissue culture: About 21 days;

Growth rate: Moderate to rapid;

Crop time: About 12 to 16 weeks to finish during lengthening spring days from an established 25 mm tissue culture plug to a 65 mm diameter container;

Rooting habit: Fleshy, lightly branching, with roots up to 30 cm long;

Root color: Nearest RHS 158C depending on soil type;

Plant shape and habit: Succulent herbaceous perennial with basal rosettes of up to about 104 fleshy leaves radially emerging and arching from central rhizome, producing a symmetrical, low, rounded mound;

Plant size: Foliage height about 38.0 cm tall from soil line to the top of the foliage and 74.0 cm wide near soil level, scape to about 170 cm tall and flowering in upper about 96 cm tall and 16.0 cm wide at the widest flowers;

Foliage description: Lanceolate; simple; sarcous; slightly fibrous; glabrous, smooth and slightly glaucous adaxial and abaxial; becoming slightly lustrous adaxial and abaxial; margins finely dentate with firm teeth; apex acute with sharp semi-flexible mucro; base truncate, sessile, clasping; not sinuate; slightly concavo-convex and slightly arching with maturity;

Leaf size: To about 41.0 cm long, about 3.5 cm wide about one-third away from base, 3.8 cm wide at base, 1.0 cm thick and 1.0 cm deep; average about 37.0 cm long, 3.3 cm wide about one-third away from base and 0.8 cm thick; typically bi-laterally symmetrical; spots of variable sizes from about 1.0 mm diameter to about 18.0 mm long and 12.0 mm across, frequently overlapping; teeth to about 1.0 mm long and 1.0 mm across at base;

Foliage fragrance: None observed;

Cauline bracts: About 27 per scape below flowers and one at each branch; lanceolate; simple; sarcous, glabrous; margins finely dentate with firm teeth to about 0.5 mm long; apex narrowly acute with semi-flexible mucro to about 4.5 mm long; base truncate, sessile, clasping; typically adpressed in proximal two-thirds; to about 21.0 cm long and about 2.8 cm wide near center, decreasing distally;

Leaf blade and bract color:

*Adaxial* (*young*).—Between RHS 137B and RHS 189B with spots nearest RHS 137A with faint blush of nearest RHS N187B.

*Abaxial* (*young*).—Between RHS 189A and RHS 189B with spots nearest RHS 137B.

*Adaxial* (*mature*).—Low ultraviolet light blend nearest RHS N138B and N138C, with spots of nearest RHS NN137A; high ultraviolet light nearest RHS N138A with faint blush of nearest RHS 182B, and spots of nearest RHS N187A.

*Abaxial* (*mature*).—Low ultraviolet light between RHS 138B and RHS 191B at the longitudinal center, the edges nearest RHS N138C, nearest RHS 146C near proximal center and with variable spots of nearest RHS 146B, RHS 137A and RHS NN137C; high ultraviolet light between RHS 146D and RHS 147A proximally, distally between RHS 138B and RHS 194B with spots variable of nearest RHS 146C and RHS 187A.

*Marginal teeth*.—Mature adaxial and abaxial distally between RHS 175A and RHS 183A; adaxial and abaxial proximal portion and on younger foliage nearest RHS NN155A becoming nearest RHS 172C distally as developing.

Mucro: Semi-flexible; sharp; straight, about 5.0 mm long and 0.5 mm across;

Mucro color: On young leaves nearest RHS 164D maturing to between RHS 177B and RHS 165A;

Petiole: Sessile;

Veins: Parallel; not distinct;

Peduncle: Terete; glaucous; glabrous; stiff; strong; upwardly; heavily branched with about 33 branches; about 170.0 cm long and to 1.7 cm diameter at base and 1.3 cm diameter below first branches;

Branches: Cylindrical distally, applanate proximally; slightly glaucous; glabrous; to about 6.0 cm long and about 0.3 cm thick and 0.8 cm across at base; branch aspect upwardly and outwardly, about 60 degrees above horizontal;

Peduncle color: Nearest RHS 147A with moderate mottling of nearest RHS 187A;

Pedicel: To about 7.0 mm long and 3.0 mm diameter; terete; glaucous; glabrous; stiff; strong;

Pedicel color: Between RHS 138A and RHS 138B;

Buds one day prior to opening: Elongated globose; about 40 mm long and about 8 mm across at bulb, ovary portion about 11.0 mm long and about 5.0 mm diameter, bulb about 2.6 cm long; rounded apex; ovary portion smooth and lustrous;

Bud color: Tepal portion nearest RHS 146D and heavily maculate to nearly solid with between RHS 178A and RHS 183A, ovary portion between RHS 147B and RHS 138A;

Flower description: Perfect; incomplete; actinomorphic; about 5.5 cm long to exserted anthers and pistil and opening to about 3.4 cm across at outside of tepals before beginning to recurve; corolla to about 2.2 cm long and 2.8 cm wide when fully recurved; lasting about 3 to 4 days per flower; flowering period about three to four weeks once plant is mature, approximately three-years-old; producing abundant nectar;

Inflorescence: Approximately 150 flowers per scape; aspect upright; flowering portion about 96.0 cm tall and about 18.0 cm across;

Flower fragrance: None detected;

Tepals: Six in two sets of three; lanceolate; glabrous and lustrous adaxial and abaxial; acute apex, about 32.0 mm long, fused in basal 14.0 mm, free in distal 18.0 mm and about 6.0 mm wide just above fusion; recurved 270° to 360°;

Tepal color: Outer tepal set adaxial basal one-third nearest RHS 145C, distal portion nearest RHS 151A when first opening and nearest RHS 145C with maturity, abaxial nearest RHS 146D with strong blush of between RHS 178A and RHS 183A; inner tepal set adaxial basal portion nearest RHS 145C when first opening and through maturity, distal portion nearest RHS 151A along margin, centers between RHS 146D and RHS 145A, when mature margin nearest RHS 145C and center between RHS 146D and 145A, abaxial margin between RHS 151A and RHS 151B, center portion nearest RHS 146D with strong blush to nearly solid between RHS 178A and RHS 183A;

Androecium: Six;

*Filaments*.—Six; cylindrical distally; straight; slightly applanate base; stiff and straight; about 36.0 mm long and 1.5 mm across and 1.0 mm thick at base; color nearest RHS 158B heavily maculate with nearest RHS 183A.

*Anther*.—Dorsifixed; longitudinal; straight, oblong; about 15.0 mm long and 2.0 mm across and 1.5 mm thick before opening; color nearest RHS 153A and heavily maculate with nearest RHS 183A.

*Pollen*.—Abundant; color nearest RHS 14B.

Gynoecium: Single; 55.0 mm long;

*Style*.—40.0 mm long and 2.5 mm diameter at base; color between RHS 162D and RHS 158B heavily maculate with nearest RHS 183A.

*Stigma*.—Turbinate, apex tri-lobed; distally puberulent; about 1.5 mm tall and 2.0 mm across top; color nearest RHS 158B.

*Ovary*.—Inferior; oblong; about 13.0 mm long and 6.0 mm across; surface smooth; color between RHS 138A and RHS 146B.

Fruit: Not yet observed;

Seed: Not yet observed;

Disease resistance: x *Mangave* 'Maverick' has not been observed to be resistant to diseases common to other x *Mangave* beyond that which is normal for *Agave* or *Manfreda*. The plant is xeromorphic and survives well with minimal water once established. Hardiness at least from USDA zone 9 to 11. Full extent of winter hardiness has not been tested.

I claim:

1. A new and distinct cultivar of ornamental X *Mangave* plant named 'Maverick' as herein described and illustrated.

* * * * *